United States Patent [19]

Plakas, Chris J.

[11] 4,144,134

[45] Mar. 13, 1979

[54] METHOD FOR DETECTION OF BACTERIAL CONCENTRATION BY LUMINESCENCE

[75] Inventor: Plakas, Chris J., Alexandria, Va.

[73] Assignee: Vitatect Corp., Alexandria, Va.

[21] Appl. No.: 764,180

[22] Filed: Jan. 31, 1977

[51] Int. Cl.² .............................................. C12K 1/04
[52] U.S. Cl. .................... 195/103.5 M; 195/103.5 L; 195/2
[58] Field of Search ................ 195/103.5 R, 103.5 M, 195/103.5 K

[56] References Cited

U.S. PATENT DOCUMENTS

| | | | |
|---|---|---|---|
| 3,616,253 | 10/1971 | D'Eustachio | 195/103.5 M |
| 3,745,090 | 7/1973 | Chappelle et al. | 195/103.5 R |
| 3,971,703 | 7/1976 | Picciolo et al. | 195/103.5 R |
| 4,013,418 | 3/1977 | Plakas | 195/127 |

Primary Examiner—Alvin E. Tanenholtz

[57] ABSTRACT

A method for detecting low levels of microbial cells in samples of fluids and degraded solids. The non-microbial reactive materials in a sample are solubilized by selective use of enzymes and the sample is filtered to remove the liquid portion of the solubilized materials while retaining the microbial cells on the filter. The microbial cells are then ruptured to expose undiluted reactive material which is then contacted with reagent material on the filter to cause a luminescent reaction. The strength of the resulting luminescence is measured as an indication of the concentration of microbial cells in the sample.

13 Claims, 1 Drawing Figure

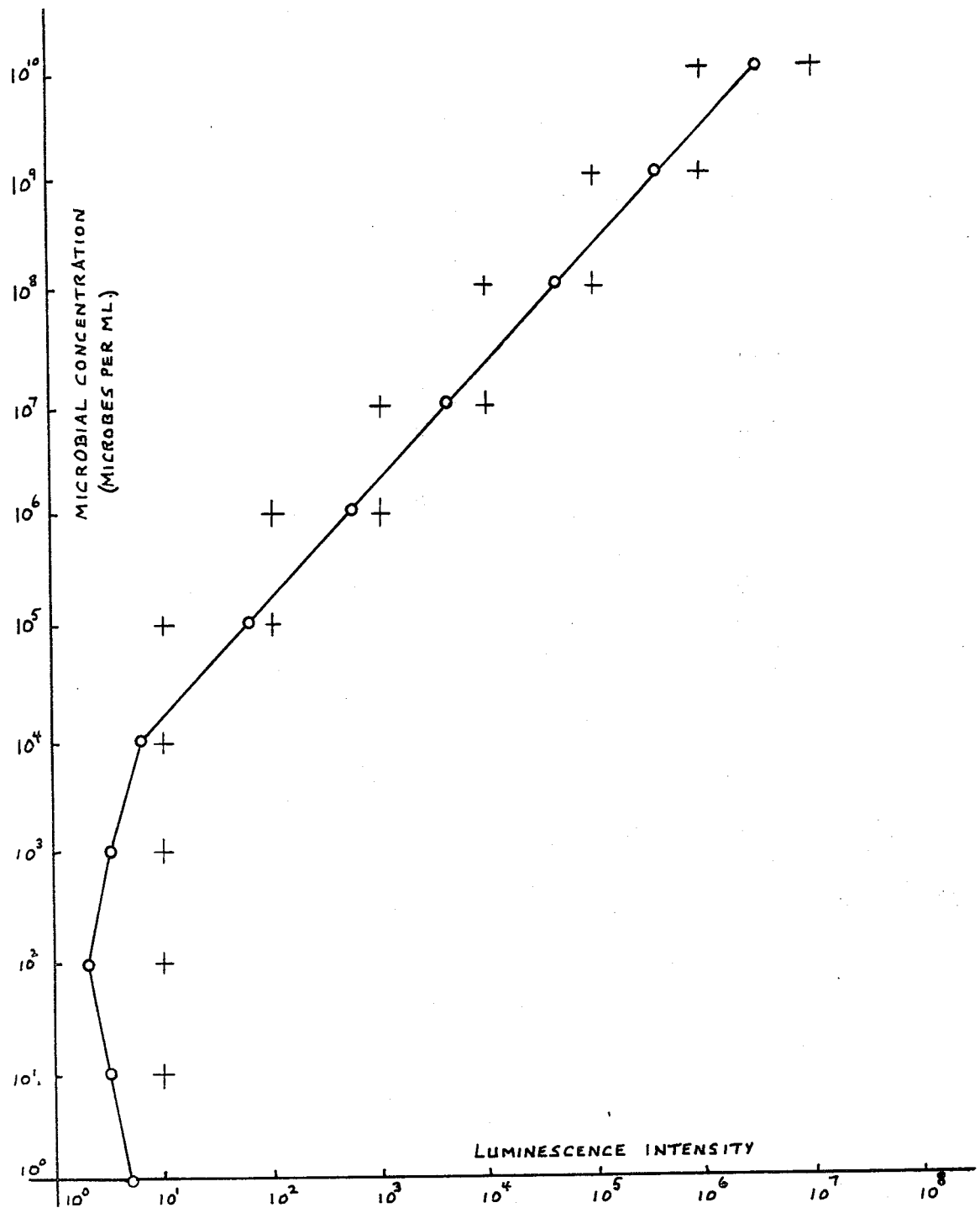

METHOD FOR DETECTION OF BACTERIAL CONCENTRATION BY LUMINESCENCE

FIELD OF THE INVENTION

The present invention relates to a method of detecting microbial cells in a sample, and more particularly this invention relates to a novel method of determining microbial reactive material by bioluminescent or chemiluminescent assay.

DESCRIPTION OF THE PRIOR ART

Current methods employed to determine microbial levels by luminescent assay generally include incubation and extraction of microbial cells in 0.1 to 1 ml volumes of aqueous sample in a cuvette, injection of reagent material into the sample or vice versa, and detection of subsequent luminescence by photodetectors. When the sample contains microbial and non-microbial cells, the method of detecting microbial cells becomes more complicated. The most serious deficiency of all volume reaction systems is that they lack sensitivity, as these methods can only detect above $10^4$ microbial cells per assay of 0.1 ml. Apparently this is caused by the dilution of reactive material in the aqueous sample, the limited supply of oxygen, which is a necessary component of the reaction process, and the presence of other reactive material in the sample. A volume-reaction system is described in Chappelle et al., U.S. Pat. No. 3,745,090. My own prior U.S. Pat. Nos. 3,690,832 and 3,940,250 and my application Ser. No. 659,534, filed Feb. 19, 1976 now U.S. Pat. No. 4,013,418, relate to the detection of reactive material from cells by luminescent reaction. My prior patents do not make it possible to detect below about $10^4$ microbial cells per 0.1 ml, nor do they make it possible to detect relatively small numbers of microbial cells among large numbers of non-microbial cells, such as contaminating microbes among the desired cells of milk or blood, for example.

SUMMARY OF THE INVENTION

The present invention overcomes these problems of the prior art devices and methods by providing a method for detecting microbial reactive material in a sample by luminescence at a very wide range of microbial concentration, including levels below that at which the luminescence emitted by the reagents themselves (i.e., endogenous light) exceeds the luminescence emitted by interaction of the reactive material and the reagent.

The present invention further overcomes these problems of the prior art devices by providing a method for selectively breaking or rupturing the non-microbial cells in the sample and rinsing away those contents of the non-microbial cells which could react with the reagent before the microbial cells are ruptured. Thus, the non-microbial reactive material is removed from the sample before tests such as are suggested by my prior patents are begun.

The invention provides a method for introducing reaction components in thin layers to assure adequate oxygen supply for the reaction. It also provides a method for degrading and filtering out non-microbial reactive material in milk, juices and other beverages, solid food products, petroleum products, body fluids and other fluids and solids. The term "degrading" includes breaking down large-scale solid structures and rupturing the cell walls of all non-microbial cellular material.

BRIEF DESCRIPTION OF THE DRAWING

The sole FIGURE shows the relationship between luminescence intensity and microbial concentration for samples of E. coli.

DESCRIPTION OF THE PREFERRED EMBODIMENTS

The presence of a relatively small number of microbial cells in a sample comprising mostly non-microbial cells may be detected by treating the sample to break down any solids present in the sample, rupturing the cell walls of all non-microbial cells to extract the non-microbial reactive material contained therein, filtering the sample to rinse all extracted material away, rupturing the cell walls of all the microbial cells to extract the microbial reactive material contained therein, preferably retaining the microbial reactive material as an undiluted residue on the filter surface, introducing a luminescence-causing reagent to saturate the extracted microbial reactive material, preferably while a residue on the filter surface, and detecting and recording an indication of the intensity of the luminescence emitted by the reaction between the reagent and the microbial reactive material. In the preferred embodiments of the invention, the cell walls of the non-microbial materials are ruptured through the use of an enzyme selected to affect the particular non-microbial cells which are present, while having minimal effect upon microbial cells.

Selected chemicals and hydrolyzing enzymes are used to degrade solid portions of the sample and release non-microbial reactive material without affecting the microbial cells. A small amount of dioctyl sodium sulfosuccinate, octyl phenoxy polyethoxethanol or any other surfactant is added to the sample to reduce surface and interfacial tension for easy filtration through a membrane filter, usually of 0.45 micron mean pore size. Rinsing liquids are used after filtration if necessary for the total removal of non-microbial reactive material. Microbial cells retained on the filter are then ruptured to extract the microbial reactive material. Extraction means are numerous; for example extraction can be achieved by forcing vapors of volatile liquids such as ether or acetone through the filter unit. Non-chemical means of extraction, such as ultrasound and heat may also be used. A heater coil inserted into the outlet plate of the filtration unit extracts cells satisfactorily. The most useful extractants in the present technique are methylene chloride, nitric acid, and dioctyl sodium sulfosuccinate. The amount of liquid extractant used varies from 0.010 to 0.025 ml. depending on the size of the area on the filter used for the extraction. For filter areas having diameters between 10 and 20 mm, 0.015 ml. of extractants medium is satisfactory. Part of the extraction liquid evaporates from the filter and part of it is absorbed in a few seconds, thus leaving the extracted reactive material undiluted on the filter surface.

Reagent is then sprayed over the filter surface to saturate the reaction area. The undiluted reactive material combines directly with the reagent for reaction. For bioluminescent assay the preferred reagent used is luciferase-luciferin mixture, which may be obtained in lyophilized state from Dupont and other suppliers. The concentration is 0.71 millimoles of luciferin with 100 units luciferase diluted in 0.5 ml. to 0.75 ml. TRIS buffer with $Mg++$ added. The TRIS buffer can be TRIS-Mg buffer from Fisher Scientific Co. or TRIZMA buffer T3753 from Sigma Co.

For chemiluminescent assay, the preferred reagent is luminol solution with sodium perborate or hydrogen peroxide. Equal parts of luminol solution ($5 \times 10^{-3}$ moles or stronger) and sodium perborate (3.846 grams per liter of $H_2O$) are mixed or enough hydrogen peroxide is added to the luminol solution to make 1% concentration.

In volume reaction systems where reactive and reagent materials are supplied in a cuvette, sensitivity is limited at the lower end to $10^4$ to $10^5$ microbial cells per assay. This is due to the endogenous light emitted by the reagent materials. For example, luciferase-luciferin enzyme (used in bioluminescent assay) and luminol (used in chemiluminescent assay) luminesce in their natural state. The amount of luminescence thus emitted is equivalent to the reaction of about $10^4$ to $10^5$ microbial cells per assay when extracted and reacted by those reagents. The cause of this background luminescence has not been explicitly determined. Some techniques have been used to reduce the intensity of this luminescence but no significant improvements have been achieved until now. The detection of reactive material which emits light in levels below endogenous light levels is achieved in the present technique when undiluted reactive material is reacted directly with reagent solution. The microbial material is extracted from the cells by chemical or other means which ruptures the cells to free the microbial reactive material without removing or diluted it. When undiluted microbial reactive material is mixed with reagent, which is supplied in excess, all molecules of the reactive material react, thus increasing quantitative accuracy.

Since the filter is exposed to the air, and as the reagent progressively spreads to the cover the area carrying reactive material, air is present to supply the oxygen demanded by reacting molecules. The thickness of the reaction layer is from 0.05 to 0.5 mm, which permits adequate oxygen supply to all reaction molecules, and thus a complete reaction occurs.

In the present method, since small amounts of reagent are used and non-microbial reactive materials are removed, the reaction curve of microbial concentration versus luminescence intensity is linear. The lowest point of linearity approximately coincides with the value of endogenous light emitted by the reagent material and depends upon the characteristics of the reagent and its preparation. Approximately 0.05 ml. of each of the reagents used in this technique emit luminescence equivalent to the reaction of 500 to 1000 microbial cells (*E. coli*). While the reagent may be purified to reduce the level of endogenous light, the curve of the reaction changes in slope at whatever may be the level of the endogenous light and continues in a linear fashion to zero concentration, as shown in the FIGURE. This phenomenon occurs because the light intensity of the reaction is below the normal intensity of the endogenous light and at the same time there is a reduction in the level of endogenous light due to the neutralization of the reagent by the microbial reactive material in the reaction in the range between zero and the normal endogenous light level. Thus the increase or decrease of microbial reactive material in the range below the normal endogenous light level controls the active amount of the enzyme, which in turn affects the intensity of endogenous light which is used as an indicator of the amount of microbial reactive material involved in the reaction. Since values of luminescence intensity in concentrations near that of the endogenous light can be double valued (i.e., cross the concentration curve twice), a double-assay filtration or double-assay dilution (See Example 12) will show the slope and the direction of the concentration curve, thus facilitating the plotting of the curve.

To perform bacteriological analysis of various food products, the samples must be degraded and forced through a membrane filter that will retain microbial cells for examination. A number of chemicals and enzymes have been tested for degradation and hydrolysis of various samples, but only a few are effective for the filtration of samples prepared for luminescence experiments.

The invention is further illustrated by the following examples. These non-limiting examples are illustrative of certain embodiments designed to teach those skilled in the art how to practice the invention and to represent the best mode contemplated for carrying out the invention.

A suitable apparatus for practicing this invention is that described in my application Ser. No. 659,534, filed Feb. 19, 1976, and in my U.S. Pat. Nos. 3,690,832 and 3,940,250.

EXAMPLES

Before the determination of microbial concentration in the sample is carried out, it is necessary to determine the enzyme effectiveness for each lot of enzymes received from the manufacturers. (See Example 11.) The enzyme effectiveness thus determined indicates the necessary enzyme concentration for microbial determination.

Determination by chemiluminescent assay is carried out using luminol solution. Luminol reagent is made by dissolving 0.855 g. of luminol (luminol-5-amino-2,3-dihydro-1,4-phthalazinedione) per 50 ml. of 1.5 N. sodium hydroxide solution (1.5 N NaOH = 60 g. NaOH per liter $H_2O$).

Determination by bioluminescent assay is similar to the chemiluminescent assay except that luciferase-luciferin enzyme solution is used instead of the luminol solution described above. Luciferase-luciferin is obtainable from the Dupont Company.

EXAMPLE 1

Milk analysis

Before starting the analysis, the free porphyrins occurring in milk and any traces of iron from milk containers must be eliminated. This is carried out as follows:

For porphyrin elimination: Add 1% by volume of hydrogen peroxide to the milk sample. Allow 2-5 minutes for degradation.

For soluble iron elimination: Add 1 part of EDTA solution to 9 parts of milk. EDTA solution is 16.8 g. ethylenediamine tetra-acetic acid in 250 ml. water.

TRITON X-100 (octyl phenoxy polyethoxyethanol), a surfactant obtainable from the Rohm and Haas Corporation, may be added to the milk sample to facilitate filtration. For a 1 ml. sample of milk, 0.1 ml. of a 1% volume solution of Triton-X is used. Dioctyl sodium sulfosuccinate can also be used as a surfactant.

Procedure

The analysis of the milk sample is carried out as follows:

(1) The pH of the milk is adjusted to 8 by adding nitric acid to decrease the pH or sodium hydroxide to increase the pH.

(2) To secure bacterial cells which are free of non-bacterial cells (white cells and proteins) contained in the milk, the sample is mixed with Rhozyme 41 protease solution. Rhozyme 41 is obtainable from Rohm and Haas Corporation. The Rhozyme 41 solution is made as follows: 5 ml. water is added to 1 g. Rhozyme 41 and 12 hours at 10° C. are allowed for complete mixing. The mixture is centrifuged at 12,000 RCF × G and the supernatant liquid is filtered through a 0.2 micron filter. 1 ml. of this Rhozyme protease solution is mixed with a 9 ml. milk sample and 10 minutes are allowed for degrading. The degrading process ruptures the non-bacterial cells. The sample may then be diluted in 4 or 5 parts of water to achieve better filtration.

(3) The sample is then filtered to remove the liquid part of the sample, which contains the former contents of the ruptured non-bacterial cells. The bacterial cells which are not affected by the Rhozyme are retained on the filter. In this filtration, the filter plunger is tightened, and then 1-5 ml. of the degraded and diluted milk sample is forced through the filter unit.

(4) The filter is then flushed with 1-5 ml. of $H_2O$.

(5) Air is then forced through the filter with a plastic syringe to remove all liquid from the filter.

(6) 0.015 ml. of 0.1 N $HNO_3$ extractant is introduced on the filter (for a filter area of 10 mm.) with a 0.05 ml. syringe using a 52 mm. needle length to avoid piercing the filter. One minute is allowed for extraction. This ruptures the bacterial (microbial) cells and exposes reactive bacterial material such as ATP (adenosine triphosphate) and hemoglobin.

(7) The filter tape is moved to the reaction position.

(8) The instrument is adjusted to zero and the photomultiplier shutter opened.

(9) A 0.05 ml. syringe containing 0.04 ml. of luminol reagent is inserted in the reagent port, and pressed carefully until the rubber stopper is pierced. The luminol reagent is injected onto the filter very gently while pressing the button to initiate measurement of the luminescence and thus a determination of the bacterial count.

This procedure as described in Steps (1) to (9) above is repeated as many times as is necessary with different ratios of enzyme solution to sample in Step (2) above in order to insure that the luminescence count is within a suitable range for accurate determination on the apparatus. The most suitable ratio of enzyme solution to sample is used for the determination of the microbial count in the samples to be analyzed.

Determinations I to IV

The procedure described above in Steps (1) through (9) was carried out five times. The microbial count was determined and an average of the five counts was taken. The microbial concentration in the sample was calculated, based upon the average value.

EXAMPLE 2

Example 1 was carried out using a luminol-perborate solution instead of the luminol reagent in Step (9). In this solution one part of luminol solution is mixed with one part of sodium perborate solution (3.846 g. $NaBO_3$ per liter $H_2O$).

EXAMPLE 3

Example 1 was carried out using a luminol-peroxide solution instead of the luminol reagent used in Step (9). In this solution, 1% by weight hydrogen peroxide solution is added to the luminol solution.

EXAMPLE 4

Example 1 is carried out through Step (8). The microbial concentration in the sample is determined by bioluminescent assay.

Luciferase-luciferin mixture obtainable from DuPont Company is used as the luminescent reagent instead of the luminol solution. The concentration used is 0.71 millimoles of luciferin with 100 units luciferase diluted in 0.5-0.75 ml. TRIS buffer.

Step (9) is carried out as in Example 1.

EXAMPLE 5

In the analysis of meat and fish products to determine the microbial concentration in the sample, a similar method can be used to that used for milk analysis as the proteins of meat and fish products are also broken down by proteases. The method of Example 1 is used, the dilution of protease to sample by weight being between 0.5 and 5% for protease of 1000 liquefying units. Alternatively the methods of Examples 2, 3, or 4 can be used.

EXAMPLE 6

The technique described above in Example 1 for detecting microbial cells present in a sample through the procedures of sample degradation, filtration, extraction, and reaction of undiluted reactive material on a filter membrane can be applied to many samples including food and dairy products, beverages, petroleum products, alcohols, and body fluids such as urine, blood, etc. Body fluids contain various non-bacterial cells such as glycoproteins and red and white blood cells which can be degraded by proteases in a similar manner to the white cells in milk. The microbial concentration in these samples can also be measured using the methods of Examples 2, 3, or 4.

EXAMPLE 7

Natural fruit juices can be treated with pectic enzymes to facilitate filtration. Pectic enzymes break down the cellular structure of fruit pieces suspended in juices, thus releasing microbial cells without affecting their structure. Pectic enzymes are commercially available from Rohm and Haas Company under the trade name of Pectinol and from other manufacturers under various trade names. The pH of the juices should be adjusted to between 3 and 4.5 and the dilution of pectic enzyme to sample by weight should be 0.2% and 1%. Before introducing the pectic enzymes to the juice sample, one part by weight of pectic enzyme powder is diluted in 10 parts of $H_2O$ and about 10 hours at 10° C. is allowed for total dilution. The dilution is then filtered through a 0.2 micron filter and one part is mixed with 10 parts natural juices and a period of time allowed for hydrolyzation which is dependent on the cellular concentration of the juices. The procedures of filtration, extraction, and reaction can be carried out as described for milk samples in Examples 1, 2, 3, or 4.

EXAMPLE 8

Vegetables and Fruits

Pectic enzymes break down cellular structure of most fruits and vegetables, thus releasing microbial cells without affecting their structure. Pectic enzymes may be adjusted to standard values for each kind of sample. The dilution of pectic enzymes for fruits and vegetables is similar to that described for fruit juices in Example 7. Since fibers of vegetables and fruits are not always degradable, pre-filtration may be necessary before testing the liquid portion of the sample. The procedures of filtration, extraction, and luminescent reaction are similar to those described in Examples 1, 2, 3, or 4.

EXAMPLE 9

To degrade starch products and release microbial cells in preparation for filtration, diastases and amylases, which are enzymes with starch liquefying activity, are used to attack the alpha-1, 4-glucosidic bonds of starch to convert to glucose, maltose, and dextrins. Both enzymes are manufactured under various trade names such as the amylase Tenase by Miles Laboratories, and the diastase Rhozyme H-39 by Rohm and Haas. Tenase has an optimum activity at pH 6 and temperature between 20° and 90° C. Rhozyme H-39 has optimum activity at pH 6.1 and temperature about 70° C.

Food products made of starch material, such as pastries and breads, can be examined for microbial concentration through filtration, extraction, and reaction processes if the starch material can be hydrolyzed. The pH of the sample must be adjusted to 6 before mixing with the liquefying solution. One part by weight of diastase or amylase is mixed with 10 parts $H_2O$ and 2 hours at 10° C. are allowed for mixing. The dilution is filtered through a 0.2 micron filter to remove any microbial cells. One part of the dilution by weight is mixed with 100 parts of the starch sample. Dry concentration of enzyme to starch, for example flour, should be 0.05 grams to 100 grams. Since the preferred use of the present technique is for rapid quantitative detection of microbial cells, the time necessary for total liquefaction is not available. Instead the mixture is stirred well and the liquid portion is filtered through a 0.45 micron filter. If the 0.45 micron filter is too fine, the mixture is prefiltered through a 10 micron filter to separate the solid particles. Loss of any bacteria through this process is compensated for in the final reading. The procedures for extraction, and reaction are similar to those previously described in Examples 1, 2, 3 or 4.

EXAMPLE 10

Quaternary ammonium hydroxide solution can also be used to break down proteins and non-microbial cells. One ml. of 1.0 N solution solubilizes as much as 250 mg. of sample. After mixing sample and solution, 2 hours are allowed at 50° C. for degradation. The sample is then filtered through a 0.5 micron filter to retain microbial cells for extraction and reaction.

The luminescent reagent is introduced and used in the same way as is described in Examples 1, 2, 3 or 4.

EXAMPLE 11

In order to calibrate one lot of luminescence reagent for use in running these tests, a master sample of bacteria such as *E. coli* is grown. By the use of a microscope, the number of bacteria per unit volume in the master sample is determined by counting. The master sample is then diluted with the amount of water which is necessary to generate a standard sample containing $10^{10}$ bacteria per ml. of standard sample. One unit of the $10^{10}$ standard sample is withdrawn and combined with nine units of water to make a second standard sample containing $10^9$ bacteria per ml. of standard sample. This process is repeated to make nine additional standard samples of respectively $10^8$, $10^7$, $10^6$, $10^5$, $10^4$, $10^3$, $10^2$, $10^1$, and $10^0$ bacteria per ml. of standard sample. The pH of each standard sample is adjusted to 8. One ml. of the $10^{10}$ standard sample is placed on the filter and steps (5) through (9) as in Example 1 are carried out to calibrate the lot of luminol reagent used in step (9). The test is repeated for four additional one ml. test samples of $10^{10}$ standard sample, and the results of the five tests of the $10^{10}$ standard sample are averaged to obtain a luminescence intensity value for the $10^{10}$ standard sample. This average luminescence intensity value is plotted on a log-log graph of microbial concentration vs. luminescence intensity. The five tests are repeated for each of the ten additional standard samples, and the resulting average values are plotted on the log-log graph. The curve in the sole FIGURE represents the results of the calibration of one such lot of reagent. This calibration curve is used in other tests conducted with the same lot of reagent to assign bacterial count values to various luminescence intensity values.

EXAMPLE 12

A sample of unknown concentration is tested by placing a 1 ml. sample on a filter paper and carrying out steps (5) through (9) of Example 1, repeating the test four additional times, and averaging a luminescence intensity value of $3.0 \times 10^0$ is obtained in step (9), corresponding to a microbial concentration of either $1.0 \times 10^1$ or $7.0 \times 10^2$ microbes per ml. A second test is run using 2 ml. of the same sample and a luminescence intensity value of $2.5 \times 10^0$ is obtained, thereby indicating that the $1.0 \times 10^1$ concentration value was correct. (Had the second test given a luminescence intensity value of $4.00 \times 10^0$, the $7.0 \times 10^2$ value would have been the correct concentration value.)

In all of the above examples wherein multiple tests are run and averages taken, various statistical techniques can be used. Different numbers of samples can be used, and samples which are quite far from the average can be discarded. Instead of five tests, seven tests could be run, the highest and lowest values discarded, and the remaining values averaged.

In tests where more than one type of non-microbial cell is present, as with meat and vegetable soup, it may be necessary to eliminate components successively according to their progressive sensitivity to the extracting liquid. It would be necessary to remove meat (protein), potato (starch) and tomato (fruit) before testing such soup for microbes.

What is claimed is:

1. A method for detecting the presence of microbial cells in a sample comprising a mixture of microbial cells and non-microbial cells comprising the steps of:
   (A) combining the sample with an enzyme which ruptures the walls of the non-microbial cells to extract non-microbial reactive material contained therein,
   (B) removing the non-microbial reactive material extracted from the non-microbial cells by filtering said sample on a filter surface to eliminate the non-microbial reactive material from non-microbial cells and to produce a residue on the filter surface containing microbial cells, (C) rupturing the walls of the microbial cells on the filter surface to extract and retain microbial reactive material contained therein on the filter surface, (D) combining on the filter surface the microbial reactive material with a luminescence-causing reagent to generate light as a function of the amount of reactive material thus combined, and (E) detecting the amount of light thus generated on the filter surface.

2. The method of claim 1 wherein the steps A and B further comprise sequential steps for rupturing different types of non-microbial cells according to their progressive sensitivity to extracting means.

3. A method using a luminescent reaction for optically detecting the presence of microbial cells in a sample comprising a mixture of microbial and non-microbial cells comprising the steps of:

(a) rupturing non-microbial cells in the sample using an enzyme in order to facilitate filtration and to extract non-microbial reactive material from non-microbial cells from said sample without affecting microbial cells, (B) filtering said sample on a filter surface to eliminate the non-microbial reactive material from non-microbial cells and to produce a residue on the filter surface containing microbial cells, (C) rupturing microbial cells in said residue while on said filter surface to extract undiluted microbial reactive material on said filter surface, (D) bringing undiluted microbial reactive material and reagent material into contact for reaction and consequent light emission, and (E) detecting and recording the amount of light thus emitted as an indication of the quantity of microbial reactive material present in said sample.

4. The method of claim 3 where the sample contains fruit or vegetable products and the enzyme is selected from the group of pectic enzymes in order to degrade the pectins present in cellular structures of such fruit or vegetable products.

5. The method of claim 3 wherein the sample contains starch and the enzyme is selected from the group of diastase enzymes in order to degrade such starch samples.

6. The method of claim 3 wherein the sample contains starch and the enzyme is selected from the group of amylase enzymes in order to degrade such starch samples.

7. The method of claim 3 wherein the sample contains proteins and the enzyme is selected from the group of protease enzymes in order to solubilize such proteins.

8. The method of claim 3 wherein the step of rupturing microbial cells in said residue while on said filter surface is accomplished by introducing extremely small volumes of less than 0.025 ml of extractant to rupture the microbial cells, this extractant being evaporated and absorbed by the filter material and thus leaving no liquid to dilute the extracted material.

9. The method of claim 3 wherein rupturing microbial cells in said residue while on said filter surface is accomplished by introducing gas and vapor fumes into the filter unit to rupture the microbial cells in a dry environment.

10. The method of claim 3 wherein the step of filtering said sample on a filter surface comprises filtering to remove all liquid portion of said sample and rinsing the residue to remove all non-microbial reactive material, in order to retain on the filter surface a sample residue containing microbial cells.

11. The method of claim 3 wherein bringing microbial reactive material and reagent material into contact comprises applying liquid reagent evenly over the undiluted microbial reactive material carried on the filter.

12. The method of claim 3 wherein bringing microbial reactive material and reagent material into contact further comprises introducing reagent and microbial reactive material in thin layers to allow oxygen supply to all microbial reactive molecules during the reaction.

13. The method of claim 3 wherein the amount of light is below the level of endogenous light of the reagent.

* * * * *